United States Patent
Mori et al.

(10) Patent No.: US 11,278,623 B2
(45) Date of Patent: *Mar. 22, 2022

(54) NON-AQUEOUS PATCH

(71) Applicants: ITOCHU CHEMICAL FRONTIER Corporation, Tokyo (JP); OISHI KOSEIDO CO., LTD., Saga (JP)

(72) Inventors: Tatsuya Mori, Saga (JP); Naoyuki Saida, Saga (JP)

(73) Assignees: ITOCHU CHEMICAL FRONTIER Corporation, Tokyo (JP); OISHI KOSEIDO CO., LTD., Saga (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/941,429

(22) Filed: Jul. 28, 2020

(65) Prior Publication Data

US 2021/0077626 A1 Mar. 18, 2021

Related U.S. Application Data

(60) Continuation of application No. 15/891,915, filed on Feb. 8, 2018, now Pat. No. 10,765,749, which is a (Continued)

(51) Int. Cl.
*A61K 47/12* (2006.01)
*A61K 31/167* (2006.01)
*A61K 9/70* (2006.01)

(52) U.S. Cl.
CPC ............ *A61K 47/12* (2013.01); *A61K 9/7053* (2013.01); *A61K 31/167* (2013.01)

(58) Field of Classification Search
None
See application file for complete search history.

(56) References Cited

U.S. PATENT DOCUMENTS

| 4,685,907 A | 8/1987 | Agren et al. |
| 4,946,853 A | 8/1990 | Bannon et al. |

(Continued)

FOREIGN PATENT DOCUMENTS

| EP | 1125578 A1 | 8/2001 |
| EP | 1238664 A1 | 9/2002 |

(Continued)

OTHER PUBLICATIONS

Bica, K. et al., "Liquid forms of pharmaceutical co-crystals: exploring the boundaries of salt formation", Chem. Commun., 47: 2267-2269 (2011).

(Continued)

*Primary Examiner* — Melissa S Mercier
(74) *Attorney, Agent, or Firm* — Cooley LLP

(57) ABSTRACT

Non-aqueous patches comprising lidocaine, which is not dissolved and is present in a crystalline state, have poor permeability to the skin. Therefore, non-aqueous patches have a high concentration of lidocaine. It is pointed out that lidocaine has an adverse effect on the heart. Prolonged use of a high concentration of lidocaine causes side effects, such as shock, rubor, and irritating sensation. External preparations comprising more than 5 mass % of lidocaine are designated as powerful drugs, and cannot be used as household (nonprescription) medicine. Provided is a non-aqueous patch that is effective to relieve muscle pain, the non-aqueous patch comprising lidocaine and/or its reactant, and a dissolving agent composed of an organic acid and a polyalcohol, which are contained in a base.

18 Claims, 2 Drawing Sheets

Related U.S. Application Data continuation of application No. 15/646,744, filed on Jul. 11, 2017, now Pat. No. 9,931,403, which is a continuation of application No. 15/065,075, filed on Mar. 9, 2016, now Pat. No. 9,925,264, which is a division of application No. 14/116,730, filed as application No. PCT/JP2011/060781 on May 10, 2011, now Pat. No. 9,283,174.

(56) References Cited

U.S. PATENT DOCUMENTS

| | | | |
|---|---|---|---|
| 5,098,417 A | 3/1992 | Yamazaki et al. | |
| 5,234,957 A | 8/1993 | Mantelle | |
| 5,411,738 A | 5/1995 | Hind | |
| 5,478,567 A | 12/1995 | Nakagawa et al. | |
| 5,527,536 A | 6/1996 | Merkle et al. | |
| 5,536,263 A | 7/1996 | Rolf et al. | |
| 5,589,180 A | 12/1996 | Hind | |
| 5,601,838 A | 2/1997 | Hind | |
| 5,601,839 A | 2/1997 | Quan et al. | |
| 5,618,274 A | 4/1997 | Rosenthal | |
| 5,709,869 A | 1/1998 | Hind | |
| 5,741,510 A | 4/1998 | Rolf et al. | |
| 5,773,022 A | 6/1998 | Nyqvist-Mayer et al. | |
| 5,804,213 A | 9/1998 | Rolf | |
| 5,827,529 A | 10/1998 | Ono et al. | |
| 5,830,497 A | 11/1998 | Yamanaka et al. | |
| 5,834,010 A | 11/1998 | Quan et al. | |
| 5,891,919 A | 4/1999 | Blum et al. | |
| 5,979,447 A | 11/1999 | Al-Falahe | |
| 5,985,317 A | 11/1999 | Venkateshwaran et al. | |
| 6,096,333 A | 8/2000 | Rolf et al. | |
| 6,096,334 A | 8/2000 | Rolf et al. | |
| 6,120,792 A | 9/2000 | Juni | |
| 6,211,425 B1 | 4/2001 | Takayasu et al. | |
| 6,221,383 B1 | 4/2001 | Miranda et al. | |
| 6,251,100 B1 | 6/2001 | Flock et al. | |
| 6,255,502 B1 | 7/2001 | Penkler et al. | |
| 6,264,927 B1 | 7/2001 | Monahan | |
| 6,264,981 B1 | 7/2001 | Zhang et al. | |
| 6,297,290 B2 | 10/2001 | Guise et al. | |
| 6,299,902 B1 | 10/2001 | Jun et al. | |
| 6,361,790 B1 | 3/2002 | Rolf et al. | |
| 6,365,178 B1 | 4/2002 | Venkateshwaran et al. | |
| 6,383,511 B1 | 5/2002 | Cassel | |
| 6,410,048 B1 | 6/2002 | Fotinos | |
| 6,455,066 B1 | 9/2002 | Fischer et al. | |
| 6,461,644 B1 | 10/2002 | Jackson et al. | |
| 6,469,227 B1 | 10/2002 | Cooke et al. | |
| 6,528,086 B2 | 3/2003 | Zhang | |
| 6,546,281 B1 | 4/2003 | Zhang et al. | |
| 6,562,363 B1 | 5/2003 | Mantelle et al. | |
| 6,580,011 B1 | 6/2003 | Jennings-Spring | |
| 6,645,521 B2 | 11/2003 | Cassel | |
| 6,689,380 B1 | 2/2004 | Marchitto et al. | |
| 6,746,689 B2 | 6/2004 | Fischer et al. | |
| 6,825,203 B2 | 11/2004 | Pasternak et al. | |
| 6,830,758 B2 | 12/2004 | Nichols et al. | |
| 6,953,590 B1 | 10/2005 | Owaki et al. | |
| 6,995,819 B2 | 2/2006 | Kaneko et al. | |
| 6,998,109 B1 | 2/2006 | Pearson et al. | |
| 7,094,228 B2 | 8/2006 | Zhang et al. | |
| 7,127,285 B2 | 10/2006 | Henley et al. | |
| 7,166,641 B2 | 1/2007 | Lee et al. | |
| 7,179,477 B2 | 2/2007 | Gupta | |
| 7,288,265 B1 | 10/2007 | Rolf | |
| 7,655,038 B2 | 2/2010 | Luthra et al. | |
| 7,655,687 B2 | 2/2010 | Hamamoto et al. | |
| 7,695,733 B2 | 4/2010 | Zasler et al. | |
| 7,728,188 B2 | 6/2010 | Tippett | |
| 7,754,240 B2 | 7/2010 | Staniforth et al. | |
| 7,829,099 B2 | 11/2010 | Woeller et al. | |
| 7,904,146 B2 | 3/2011 | Anderson et al. | |
| 7,910,135 B2 | 3/2011 | St. John et al. | |
| 7,921,999 B1 | 4/2011 | Kimball | |
| 7,993,654 B2 | 8/2011 | Woeller et al. | |
| 8,231,906 B2 | 7/2012 | Mantelle | |
| 8,722,065 B2 | 5/2014 | Ishibashi et al. | |
| 9,283,174 B2 * | 3/2016 | Mori | A61P 25/02 |
| 9,925,264 B2 * | 3/2018 | Mori | A61K 47/12 |
| 9,931,403 B2 * | 4/2018 | Mori | A61K 47/12 |
| 10,765,640 B2 | 9/2020 | Mori et al. | |
| 10,765,749 B2 * | 9/2020 | Mori | A61K 47/12 |
| 2002/0045043 A1 | 4/2002 | Kuniya et al. | |
| 2002/0106402 A1 | 8/2002 | Hartwig | |
| 2003/0124174 A1 | 7/2003 | Galer | |
| 2005/0042269 A1 | 2/2005 | Tateishi et al. | |
| 2005/0260255 A1 | 11/2005 | Terahara et al. | |
| 2006/0029654 A1 | 2/2006 | Cassel | |
| 2007/0196458 A1 | 8/2007 | Zhang et al. | |
| 2009/0004255 A1 | 1/2009 | Uchida et al. | |
| 2009/0297591 A1 | 12/2009 | Chiang et al. | |
| 2009/0305068 A1 | 12/2009 | Morishita et al. | |
| 2010/0003313 A1 | 1/2010 | Suzuki et al. | |
| 2010/0029704 A1 | 2/2010 | Hanma et al. | |
| 2010/0092544 A1 | 4/2010 | Okada et al. | |
| 2010/0234471 A1 | 9/2010 | Ishibashi et al. | |
| 2011/0097384 A1 | 4/2011 | Kanios et al. | |
| 2011/0152377 A1 | 6/2011 | Hanma et al. | |
| 2012/0071511 A1 | 3/2012 | Naruse et al. | |
| 2012/0171278 A1 | 7/2012 | Takada et al. | |
| 2012/0184563 A1 | 7/2012 | Hanma | |
| 2012/0283671 A1 | 11/2012 | Shibata et al. | |
| 2016/0184432 A1 | 6/2016 | Mori et al. | |
| 2018/0177742 A1 | 6/2018 | Mori et al. | |
| 2018/0256495 A1 | 9/2018 | Hanma et al. | |
| 2020/0230073 A1 | 7/2020 | Mori et al. | |

FOREIGN PATENT DOCUMENTS

| | | |
|---|---|---|
| EP | 1293199 A1 | 3/2003 |
| EP | 2210599 A1 | 7/2010 |
| EP | 2311498 A1 | 4/2011 |
| EP | 2708229 A1 | 3/2014 |
| JP | H07215850 A | 8/1995 |
| JP | H09315964 A | 12/1997 |
| JP | H10-147521 A | 6/1998 |
| JP | 2816765 B2 | 10/1998 |
| JP | H11-049670 A | 2/1999 |
| JP | 2000-178186 A | 6/2000 |
| JP | 3159688 B2 | 4/2001 |
| JP | 2001-302501 A | 10/2001 |
| JP | 2003-191659 A | 7/2003 |
| JP | 2009-120551 A | 6/2009 |
| JP | 2009-524586 A | 7/2009 |
| JP | 2010-202663 A | 9/2010 |
| JP | 2011-521975 A | 7/2011 |
| JP | 5856153 B2 | 2/2016 |
| WO | WO-92/015289 A1 | 9/1992 |
| WO | WO-1999/015210 A2 | 4/1999 |
| WO | WO-2007/070679 A2 | 6/2007 |
| WO | WO-2009/060629 A1 | 5/2009 |
| WO | WO-2010/016219 A1 | 2/2010 |
| WO | WO-2012/153396 A1 | 11/2012 |
| WO | WO-2013/046335 A1 | 4/2013 |
| WO | WO-2017/034041 A1 | 3/2017 |
| WO | WO-2019/220420 A1 | 11/2019 |

OTHER PUBLICATIONS

Endo Pharmaceuticals, Inc., "LIDODERM—lidocaine patch 5%", [retrieved from the internet] < http://www.endo.com/File%20Library/Products/Prescribing%20Information/LIDODERM_prescribing_information.html> (2015).

Grünenthal GMBH, "Versatis 5% medicated plaster (lidocaine)", 4 pages (2015).

Haghpanah, S. et al. "Application No. 2079620rig1s000 Summary Review", Clinical Review, Cross-Discipline Team Leader, and Summary Division Director Review, NDA 207962 ZTlido Patch Complete Response Submission; Ref. ID: 4227523: 1-38. (Feb. 28, 2018) [retrieved on Nov. 15, 2019]. Retrieved from the Internet

(56) References Cited

OTHER PUBLICATIONS

<https://www.accessdata.fda.gov/drugsatfda_docs/nda/2018/207962Orig1s000SumR.pdf>.
Hoffman, M. "FDA Approves Lidocaine Patch 1.8% for Post-Herpetic Neuralgia", MD Mag: 2 pages. (Feb. 28, 2018) [retrieved on Nov. 15, 2019]. Retrieved from the Internet <https://www.mdmag.com/medical-news/fda-approves-lidocaine-patch-18-for-postherpetic-nerualgia>.
Schriever, J. "Patch adhesion and local tolerability of Transdermal Delivery Systems Requirements according to the new draft EMA Guidelines", BfArM Federal Institute for Drugs and Medical Devices: 20 pages. (May 16, 2013) [retrieved on Nov. 15, 2019]. Retrieved from the Internet <https://www.agah.eu/wp-content/uploads/Schriever_patch_adhesion_local_tolerability.pdf>.
Stahl, J. et al., "The effects of chemical and physical penetration enhancers on the percutaneous permeation of lidocaine through equine skin", BMC Veterinary Research, 10(138) (2014).
International Search Report and Written Opinion for PCT/JP2011/060781 dated Jun. 14, 2011, 10 pages.
International Search Report and Written Opinion for PCT/JP2011/072072 dated Oct. 25, 2011, 14 pages.
International Search Report and Written Opinion for PCT/JP2016/075376 dated Nov. 29, 2016, 8 pages.
International Search Report and Written Opinion for PCT/IB2019/054155 dated Oct. 15, 2019, 14 pages.
Extended European Search Report dated Oct. 22, 2014 for EP Application No. 11865320.3 filed May 10, 2011, 7 pages.
Extended European Search Report dated Sep. 14, 2015 for EP Application No. 11873101.7 filed Sep. 27, 2011, 6 pages.
Extended European Search Report dated Jun. 18, 2018 for EP Application No. 18166768.4 filed Sep. 27, 2011, 7 pages.
Extended European Search Report dated Oct. 21, 2019 for EP Application No. 19180829.4 filed May 10, 2011, 8 pages.
Inada, T., et al. "Lidocaine tape relieves pain due to needle insertion during stellate ganglion block", Canadian Journal of Anaesthesia 44(3):259-62. (Apr. 1997).
Final Office Action dated May 22, 2019 for U.S. Appl. No. 15/891,915, filed Feb. 8, 2018, 13 pages.
Non-Final Office Action dated Mar. 19, 2019 for U.S. Appl. No. 14/346,794, filed Jul. 1, 2014, 29 pages.
Final Office Action dated May 1, 2019 for U.S. Appl. No. 15/904,071, filed Feb. 23, 2018, 9 pages.
Final Office Action dated Dec. 27, 2019 for U.S. Appl. No. 14/346,794, filed Jul. 1, 2014, 14 pages.
Non-Final Office Action dated Dec. 18, 2019 for U.S. Appl. No. 15/891,915, filed Feb. 8, 2018, 7 pages.
Notice of Allowance dated Apr. 29, 2020 for U.S. Appl. No. 14/346,794, filed Jul. 1, 2014, 9 pages.
Notice of Allowance dated Apr. 29, 2020 for U.S. Appl. No. 15/891,915, filed Feb. 8, 2018, 8 pages.
Corrected Notice of Allowability dated Jun. 16, 2020 for U.S. Appl. No. 14/346,794, filed Jul. 1, 2014, 6 pages.
Supplemental Notice of Allowability dated Jun. 18, 2020 for U.S. Appl. No. 14/346,794, filed Jul. 1, 2014, 2 pages.
Non-Final Office Action dated Jul. 15, 2020 for U.S. Appl. No. 16/588,766, filed Sep. 30, 2019, 11 pages.
United States Patent and Trademark Office, Non-Final Office Action for U.S. Appl. No. 16/941,429, dated Jun. 3, 2021, 6 pages.

* cited by examiner

FIG. 3

| Example No. component | Example 1 | Example 2 | Example 3 | Example 4 | Example 5 | Example 6 | Comparative Example 1 | Comparative Example 2 |
|---|---|---|---|---|---|---|---|---|
| styrene-isoprene-styrene block copolymer | 18 | 15 | 18 | 20 | 18 | 20 | 20 | 18 |
| polyisobutylene | 5 | 10 | 10 | 8 | 5 | 8 | 5 | 10 |
| Hydrogenated rosin ester | 12 | - | - | 20 | 12 | - | 15 | - |
| terpene resin | 10 | 20 | 20 | - | 10 | 20 | 5 | 20 |
| liquid paraffin | 43.8 | 48.3 | 45.9 | 48.2 | 39.1 | 49.165 | 48.2 | 51.3 |
| isostearic acid | - | 1.5 | 1.8 | 1.5 | 2.1 | 1.4 | - | - |
| olein acid | 2 | - | - | - | - | - | - | - |
| dipropylene glycol | - | - | 0.5 | - | 7 | 0.035 | - | - |
| 1,3-butylene glycol | 1.5 | 1.5 | - | 1 | - | - | - | - |
| light anhydrous silicic acid | 0.5 | 0.5 | 0.5 | 0.5 | 0.5 | 0.5 | 0.5 | 0.5 |
| dibutylhydroxytoluene | 0.2 | 0.2 | 0.3 | 0.3 | 0.3 | 0.2 | 0.3 | 0.2 |
| lidocaine | 7 | 3 | 2 | 0.5 | 7 | 0.7 | 2 | 3 |
| Polysorbate 80 | - | - | - | - | - | - | 4 | - |
| Total | 100 | 100 | 100 | 100 | 100 | 100 | 100 | 100 |

FIG. 4

| Sample | Example 1 | Example 2 | Example 3 | Example 4 | Example 5 | Example 6 | Comparative Example 1 | Comparative Example 2 |
|---|---|---|---|---|---|---|---|---|
| Ball tack score | 18 | 19 | 19 | 20 | 18 | 20 | 9 | 18 |

NON-AQUEOUS PATCH

RELATED APPLICATIONS

This application is a continuation of U.S. application Ser. No. 15/891,915, filed on Feb. 8, 2018, now U.S. Pat. No. 10,765,749, issued on Sep. 8, 2020, which is a continuation of U.S. application Ser. No. 15/646,744, filed on Jul. 11, 2017, now U.S. Pat. No. 9,931,403, issued on Apr. 3, 2018, which is a continuation of U.S. application Ser. No. 15/065,075, filed on Mar. 9, 2016, now U.S. Pat. No. 9,925,264, issued on Mar. 27, 2018, which is a divisional of U.S. application Ser. No. 14/116,730, filed on Feb. 3, 2014, now U.S. Pat. No. 9,283,174, issued on Mar. 15, 2016, which is a U.S.C. § 371 national stage filing of International Application No. PCT/JP2011/060781, filed May 10, 2011, which designated the United States. The entire contents of these applications are explicitly incorporated by reference in their entirety.

TECHNICAL FIELD

The present invention relates to a non-aqueous patch for medical and home use using lidocaine.

BACKGROUND ART

Lidocaine is used for the purpose of local anesthesia or topical anesthesia. The usage form of lidocaine is an external preparation comprising lidocaine or a patch comprising lidocaine. Examples of external preparations include ointment, cream, jelly, spray, etc., which are used, for example, for topical anesthesia of the skin in the treatment of postherpetic neuralgia. Examples of patches include aqueous base patches (cataplasms) and non-aqueous patches (tapes).

An example of aqueous base patches is Lidoderm (registered trademark of Endo Pharmaceuticals (U.S.)), which is mainly used for topical anesthesia of the skin in the treatment of postherpetic neuralgia, and is also used to relieve pain in various muscles. Aqueous base patches have thick plasters because they contain moisture; therefore, aqueous base patches are poorly compatible with the skin. Moreover, due to very little adhesion, aqueous base patches are difficult to be attached to the skin for a long period of time. Furthermore, the vaporization of moisture problematically causes changes in adhesion and physical properties. Additionally, in order to make lidocaine permeate into the muscle, it is necessary to dissolve lidocaine, and moisture is thus required to dissolve lidocaine.

Next, as a non-aqueous patch, for example, Patent Japanese Patent No. 3159688 (patent Document 1) discloses a technique for alleviating postherpetic neuralgia, in which 5 to 30 wt. % of lidocaine is added as a local anesthetic. Japanese Unexamined Patent Publication No. 7-215850 (Patent Document 2) discloses a technique relating to a percutaneous absorption tape for local anesthesia comprising 5 to 100 wt. % of lidocaine. Japanese Unexamined Patent Publication No. 9-315964 (Patent Document 3) and Japanese Unexamined Patent Publication No. 2001-392501 (Patent Document 4) disclose techniques relating to a patch comprising 0.5 to 5 mass % of lidocaine. WO 2009/060629 (Patent Document 5) discloses a technique relating to a patch comprising 10 to 40 mass % of lidocaine. These non-aqueous patches have poor permeability to the skin because the lidocaine is not dissolved and is present in a crystalline state.

In addition, the technique disclosed in Patent Document 5 uses a high concentration of lidocaine. It is pointed out that lidocaine has an adverse effect on the heart. Prolonged use of a high concentration of lidocaine causes side effects, such as shock, rubor, and irritating sensation. External preparations comprising more than 5 mass % of lidocaine are designated as powerful drugs, and cannot be used as household (nonprescription) medicine.

In contrast, the techniques disclosed in Patent Documents 3 and 4 use a small amount of lidocaine, and can be used for household use; however, even after the small amount of lidocaine is completely dissolved, the lidocaine cannot be stably released over a long period of time (e.g., 12 hours or more) and cannot permeate into the skin. Thus, there is a problem with the pain-relieving effect.

SUMMARY OF INVENTION

Technical Problem

Using lidocaine, which has the effect of relieving pain in the skin when a needle is punctured, the present inventors focused on the development of a non-aqueous patch for relieving muscular pain through the skin.

For this purpose, the present inventors first focused on the use of a small amount of lidocaine, not a high concentration of lidocaine, in the plaster, and on the complete dissolution of lidocaine so that the small amount of lidocaine is percutaneously absorbed stably over a long period of time and permeates into the muscle. When these requirements are satisfied, lidocaine can be used as a non-aqueous patch that can relieve muscular pain over a long period of time.

Solution to Problem

Accordingly, in the present invention, a dissolving agent composed of an organic acid and a polyalcohol was used, and 0.5 to 7 mass % of lidocaine and/or its reactant was mixed in a plaster, thereby producing a non-aqueous patch in which the lidocaine is completely dissolved, and which is effective to relieve various muscle pains over a long period of time. The amount of lidocaine and/or its reactant in the plaster is preferably 0.1 to 1 mg/cm$^2$.

The non-aqueous patch is required to have a low plaster mass. When the size of one patch is 14×10 cm, the plaster mass is 0.84 to 2.8 g. Because the lidocaine content of the plaster is 0.5 to 7 mass %, the amount of lidocaine per patch can be kept as 196 mg or less.

In order to make lidocaine present uniformly and stably in the plaster for effective use, the lidocaine content is set to be 0.5 to 7 mass %. The reason for this is that when the lidocaine content is less than 0.5 mass %, the effect of relieving various muscle pains is low, and the desired effectiveness cannot be achieved. In contrast, when the lidocaine content is more than 7 mass %, a large amount of dissolving agent is required to ensure the release of lidocaine. The adhesion of the patch is thereby reduced, and the physical properties of the patch cannot be maintained, failing to cause the patch to be sufficiently attached to the affected part. Another reason is that the lidocaine content is desired to be low.

According to the present invention, a small amount of lidocaine is efficiently dissolved, and thereby the lidocaine can be released stably and reliably over a long period of time.

Particularly, the present invention is focused on a dissolving agent that can efficiently dissolve lidocaine over a long period of time, revealing that a dissolving agent composed of a mixture of an organic acid and a polyalcohol allows continuous and reliable dissolution of lidocaine.

Examples of organic acids include acetic acid, oleic acid, isostearic acid, etc.

Examples of polyalcohols include 1,3-butylene glycol, propylene glycol, dipropylene glycol, polyethylene glycol, glycerin, etc.

The most effective proportion of dissolving agent and lidocaine is 0.5 to 5 mass % of dissolving agent relative to 1 mass % of lidocaine. In this proportion, lidocaine can be stably mixed in a dissolved state, increasing the release rate of the lidocaine to the skin, and causing the drug to effectively permeate into the muscle. Here, the reason for this proportion, i.e., 0.5 to 5 mass % of dissolving agent relative to 1 mass % of lidocaine, is as follows. When the amount of dissolving agent is less than 0.5 mass %, lidocaine cannot be stably dissolved and cannot therefore be favorably released. In contrast, when the amount of dissolving agent is more than 5 mass %, the adhesion of the patch decreases, and sufficient attaching power to the skin cannot be achieved.

Although general starting materials for non-aqueous patches can be used for the plaster, the patch can maintain moderate flexibility by using an elastomer as the base. As the elastomer usable as the base, for example, isoprene rubber, polyisobutylene, and styrene isoprene rubber are preferably used. The amount of elastomer is preferably 10 to 50 mass %, and more preferably 20 to 40 mass %, based on 100 mass % of the plaster.

Further, a tackifier resin for increasing adhesive power can be freely added. Usable examples thereof include rosin-based resin, synthetic petroleum resin, terpene resin, phenol resin, alicyclic petroleum resin and other resins that are generally used in patches. Polybutene or liquid paraffin may be added as a softener, and menthol, camphor, or the like may be added as a skin stimulant. Moreover, anhydrous silicic acid, zinc oxide, or other inorganic substances, zinc stearate, polyvinylpyrrolidone, or the like can be used as a regulator. Furthermore, antioxidants, UV absorbers, preservatives, sequestrants, and other additives that are designed to prevent the degradation of preparations may be used.

The plaster prepared by mixing these starting materials is held by a substrate comprising nonwoven fabric, woven fabric, knitted fabric, film, or a combination thereof, which can be generally used for patches. As a peeling film covering the plaster surface, a film moderately subjected to a mold release treatment is generally used. Since the drug may be adsorbed to the substrate or peeling film, polyester is generally used as their material; however, any materials can be used unless they cause problems.

The mass of the plaster is preferably in the range of 60 to 200 g/m$^2$, and more preferably 80 to 180 g/m$^2$. When the plaster mass is less than 60 g/m$^2$, it is necessary to increase the proportion of lidocaine to the entire plaster, in order to maintain the sufficient efficacy of lidocaine. In this case, however, lidocaine is not sufficiently dissolved and is crystallized; the crystallized lidocaine cannot be efficiently transferred to the skin. Additionally, it is difficult to control the adhesion of the patch, and the plaster is not flexible against the skin and fails to maintain moderate adhesion. In contrast, when the plaster mass is more than 200 g/m$^2$, the plaster is so heavy that plaster dripping easily occurs.

The method of producing the non-aqueous patch of the present invention may be a general method that is conventionally used, such as a hot melt method or a solvent method.

Advantageous Effects of Invention

The non-aqueous patch of the present invention allows the lidocaine in the plaster to ensure a release rate of 10% or more after the patch is attached to the skin for 12 hours. Moreover, the non-aqueous patch with a low lidocaine content does not lead to abnormal skin penetration or rapid increase in blood levels after a long period of attachment or in the damaged skin, etc., and results in fewer side effects. Thus, the non-aqueous patch has efficiency and safety as a patch for use in relieving various muscle pains.

Furthermore, in spite of a low lidocaine content, the non-aqueous patch can be used for topical anesthesia of the skin, because the lidocaine has good solubility.

BRIEF DESCRIPTION OF DRAWINGS

FIG. 3 shows a table summarizing examples of formulations disclosed herein.

FIG. 4 shows a table summarizing ball tack scores for various examples disclosed herein.

DESCRIPTION OF EMBODIMENTS

Figure 1:
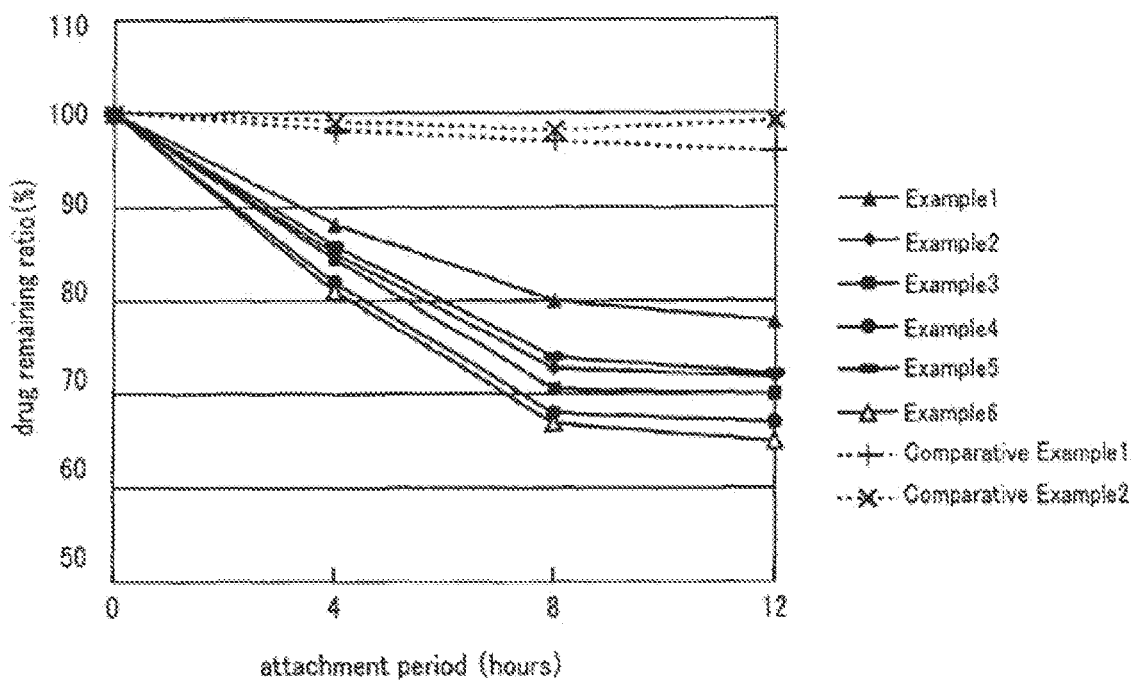
FIG. 1 is a graph showing the ratio of the remaining drug.

Examples of the present invention are summarized in a table shown in FIG. 3.

Example 1

Styrene-isoprene-styrene block copolymer ("Kraton D1161", produced by Kraton JSR Elastomers K.K.): 18 mass %

Polyisobutylene (trade name "Himol 6H", produced by JX Nippon Oil & Energy Corporation): 5 mass %

Hydrogenated rosin ester (trade name "Pinecrystal KE-311", produced by Arakawa Chemical Industries, Ltd.): 12 mass %

Terpene resin (trade name "YS resin 1150N", produced by Yasuhara Chemical Co., Ltd.): 10 mass %

Lidocaine: 7 mass %

1,3-butylene glycol (produced by Daicel Chemical Industries, Ltd.): 1.5 mass %

Oleic acid ("Purified Oleic Acid", produced by NOF Corporation): 2 mass %

Liquid paraffin (trade name "Hicall", produced by Kaneda Corporation): 43.8 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.2 mass %

The production method using these materials according to above formulation was as follows. The styrene-isoprene-styrene block copolymer, polyisobutylene, hydrogenated rosin ester, terpene resin, light anhydrous silicic acid, dibutylhydroxytoluene, and liquid paraffin were placed in a dissolution mixer and dissolved under heating at 150° C. A solution separately prepared by mixing the lidocaine, 1,3-butylene glycol, and oleic acid, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 140 g/m$^2$. A polyester woven fabric was pasted thereto and cooled. The resultant was then cut into a rectangle (about 14 cm×10 cm). In this preparation, the proportion of lidocaine and dissolving agent was 1:0.5 by mass ratio.

Example 2

Styrene-isoprene-styrene block copolymer ("Kraton D1161", produced by Kraton JSR Elastomers K.K.): 1.5 mass %
Polyisobutylene (trade name "Himol 6H", produced by JX Nippon Oil & Energy Corporation): 10 mass %
Terpene resin (trade name "YS resin 1150N", produced by Yasuhara Chemical Co., Ltd.): 20 mass %
Liquid paraffin (trade name "Hicall", produced by Kaneda Corporation): 48.3 mass %
Isostearic acid (produced by Kokyu Alcohol Kogyo Co., Ltd.): 1.5 mass %
Lidocaine: 3 mass %
1,3-butylene glycol (produced by Daicel Chemical Industries, Ltd.): 1.5 mass %
Light anhydrous silicic acid (trade name "Sylysia 350", produced by Fuji Silysia Chemical Ltd.): 0.5 mass %
Dibutylhydroxytoluene (trade name "BHT", produced by Honshu Chemical Industry Co., Ltd.): 0.2 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, lidocaine, and 1,3-butylene glycol, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 140 g/m². A polyester woven fabric was pasted thereto and cooled. The resultant was then cut into a rectangle (about 14 cm×10 cm). In this preparation, the proportion of lidocaine and dissolving agent was 1:1 by mass ratio.

Example 3

Styrene-isoprene-styrene block copolymer ("Kraton D1161", produced by Kraton JSR Elastomers K.K.): 18 mass %
Polyisobutylene (trade name "Himol 6H", produced by JX Nippon Oil & Energy Corporation): 10 mass %
Terpene resin (trade name "YS resin 1150N", produced by Yasuhara Chemical Co., Ltd.): 20 mass %
Liquid paraffin (trade name "Hicall", produced by Kaneda Corporation): 46.9 mass %
Isostearic acid (produced by Kokyu Alcohol Kogyo Co., Ltd.): 1.8 mass %
Dipropylene glycol (produced by NOF Corporation): 0.5 mass %
Lidocaine: 2 mass %
Light anhydrous silicic acid (trade name "Sylysia 350", produced by Fuji Silysia Chemical Ltd.): 0.5 mass %
Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, lidocaine, and dipropylene glycol, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 140 g/m². A polyester nonwoven fabric was pasted thereto and cooled. The resultant was then cut into a rectangle (about 14 cm×10 cm). In this preparation, the proportion of lidocaine and dissolving agent was 1:1.15 by mass ratio.

Example 4

Styrene-isoprene-styrene block copolymer ("Kraton D1161", produced by Kraton JSR Elastomers K.K.): 20 mass %
Polyisobutylene (trade name "Himol 6H", produced by JX Nippon Oil & Energy Corporation): 8 mass %
Hydrogenated rosin ester (trade name "Pinecrystal KE-311", produced by Arakawa Chemical Industries, Ltd.): 20 mass %
Liquid paraffin (trade name "Hicall", produced by Kaneda Corporation): 48.2 mass %
Isostearic acid (produced by Kokyu Alcohol Kogyo Co., Ltd.): 1.5 mass %
Lidocaine: 0.5 mass %
1,3-butylene glycol (produced by Daicel Chemical Industries, Ltd.): 1 mass %
Light anhydrous silicic acid (trade name "Sylysia 350", produced by Fuji Silysia Chemical Ltd.): 0.5 mass %
Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, hydrogenated rosin ester, light anhydrous silicic acid, dibutylhydroxytoluene, and liquid paraffin were placed in a dissolution mixer and dissolved under heating at 150° C. A solution separately prepared by mixing the isostearic acid, lidocaine, and 1,3-butylene glycol, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 160 g/m². A polyester nonwoven fabric was pasted thereto and cooled. The resultant was then cut into a rectangle (about 14 cm×10 cm). In this preparation, the proportion of lidocaine and dissolving agent was 1:5 by mass ratio.

Example 5

Styrene-isoprene-styrene block copolymer ("Kraton D1161", produced by Kraton JSR Elastomers K.K.): 18 mass %
Polyisobutylene (trade name "Himol 6H", produced by JX Nippon Oil & Energy Corporation): mass %
Hydrogenated rosin ester (trade name "Pinecrystal KE-311", produced by Arakawa Chemical Industries, Ltd.): 12 mass %
Terpene resin (trade name "YS resin 1150N", produced by Yasuhara Chemical Co., Ltd.): 10 mass %
Liquid paraffin (trade name "Hicall", produced by Kaneda Corporation): 38.1 mass %
Isostearic acid (produced bye Kokyu Alcohol Kogyo Co., Ltd.): 2.1 mass %
Lidocaine: 7 mass %
Dipropylene glycol (produced by NOF Corporation): 7 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, hydrogenated rosin ester, light anhydrous silicic acid, dibutylhydroxytoluene, and liquid paraffin were placed in a dissolution mixer and dissolved under heading at 150° C. A solution separately prepared by mixing the isostearic acid, lidocaine, and dipropylene glycol, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 100 g/m$^2$. A polyester nonwoven fabric was pasted thereto and cooled. The resultant was then cut into a rectangle (about 14 cm×10 cm). In this preparation, the proportion of lidocaine and dissolving agent was 1:1.3 by mass ratio.

Example 6

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 8 mass %

Terpene resin (trade name "YS resin 1150N", produced by Yasuhara Chemical Co., Ltd.): 20 mass %

Liquid paraffin (trade name "Hicall", produced by Kaneda Corporation): 49.165 mass %

Isostearic acid (produced by Kokyu Alcohol Kogyo Co., Ltd.): 1.4 mass %

Lidocaine: 0.7 mass %

Dipropylene glycol (produced by NOF Corporation): 0.035 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.2 mass %

The production method using these materials according to the above formulation was as follows. The styrene-isoprene-Styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, lidocaine, and dipropylene glycol, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 150 g/m$^2$. A polyester nonwoven fabric was pasted thereto and cooled. The resultant was then cut into a rectangle (about 14 cm×10 cm). In this preparation, the proportion of lidocaine and dissolving agent was 1:2.05 by mass ratio.

Comparative Example 1

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 5 mass %

Hydrogenated rosin ester (trade name "Pinecrystal KE-311", produced by Arakawa Chemical Industries, Ltd.): 15 mass %

Terpene resin (trade name "YS resin 1150N", produced by Yasuhara Chemical Co., Ltd.): 5 mass %

Liquid paraffin (trade name "Hicall", produced by Kaneda Corporation): 48.2 mass %

Polysorbate 80 (produced by NOF Corporation): 4 mass %

Lidocaine: 2 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisoprene, hydrogenated rosin ester, terpene resin, light anhydrous silicic acid, dibutylhydroxytoluene, and liquid paraffin were placed in a dissolution mixer and dissolved under heating at 150° C. A solution separately prepared by mixing the Polysorbate 80 and lidocaine, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 140 g/m$^2$. A polyester nonwoven fabric was pasted thereto and cooled. The resultant was then cut into a rectangle (about 14 cm×10 cm).

Comparative Example 2

Styrene-isoprene-styrene block copolymer ("Kraton D1161", produced by Kraton JSR Elastomers K.K.): 15 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 20 mass %

Liquid paraffin (trade name "Hicall", produced by Kaneda Corporation): 51.3 mass %

Lidocaine: 3 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.2 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. The lidocaine was added thereto, and the mixture was mixed under heating at 140° C. until the mixture became homogeneous, thereby obtaining a plaster solution. The plaster solution was applied to a polyester film treated with silicon so that the plaster weight was 140 g/m$^2$. A polyester nonwoven fabric was pasted thereto and cooled. The resultant was then cut into a rectangle (about 14 cm×10 cm).

FIG. 3 summarizes the exemplary formulations in a table.

The preparations obtained in Examples 1 to 6 and Comparative Examples 1 and 2 were subjected to the following tests.

Adhesion Test

A ball tack adhesion test was performed according to the test method described in Drug Approval and Licensing Procedures in Japan. As shown in FIG. 4, Examples 1 to 6 (hereinafter referred to the "invention products") showed excellent adhesion. The adhesion of Comparative Example 1 was about half of those of the invention products. Comparative Example 2 had satisfactory adhesion, because no dissolving agent was used.

Drug Remaining Test

As shown in FIG. 1, the preparations were attached to the human skin for 4 hours, 8 hours, and 12 hours. After each time period was passed, the preparations were removed. The amount of drug remaining in each preparation was measured to determine the drug remaining ratio on the premise that the amount of drug prior to attachment was 100%.

The drug remaining ratio after attachment for 12 hours was 96 to 99% in the comparative examples, while the results of all of the invention products were 80% or less, and the amount of drug released into the human skin was 20% or more.

Blood Level Test

Figure 2:
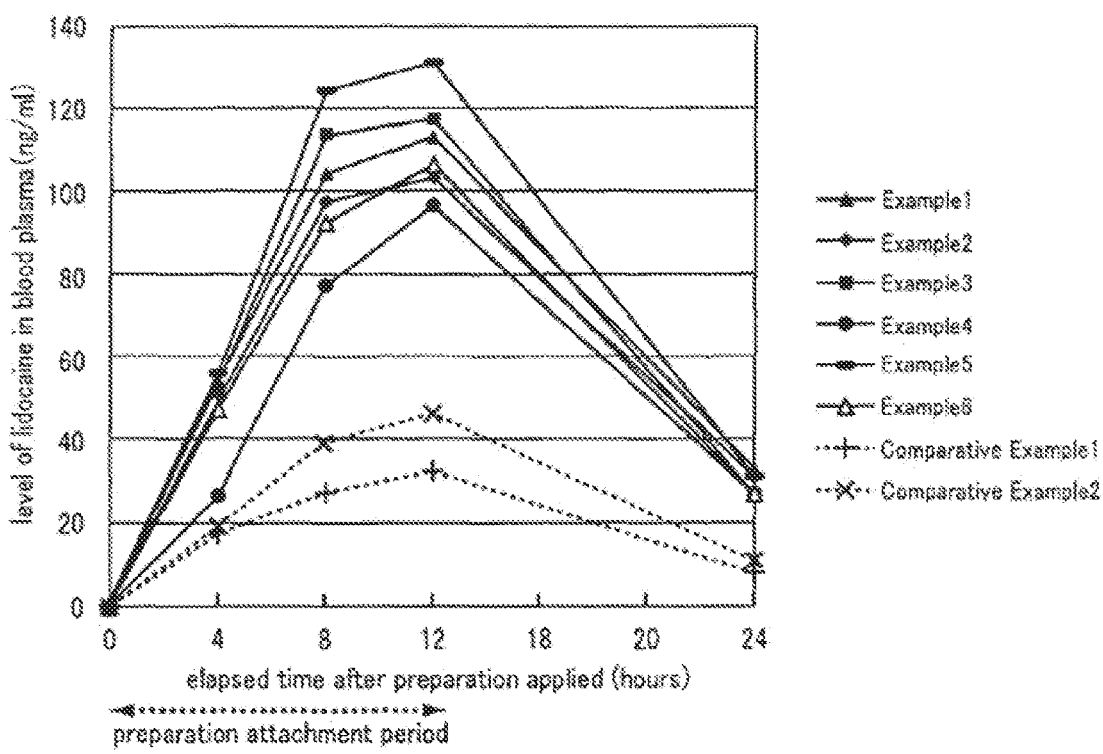
FIG. 2 is a graph showing blood levels.

The preparations were attached to the human skin for 12 hours and then removed. 4 hours, 8 hours, and 12 hours after the attachment of the preparations, and 24 hours after the removal of the preparations, the blood was extracted, and the level of lidocaine in the blood was measured. FIG. 2 is a graph showing the results.

The results reveal that the preparations comprising a dissolving agent composed of isostearic acid and dipropylene glycol showed generally good results.

The invention claimed is:

1. A method of treating pain in an individual in need thereof, comprising applying a non-aqueous patch to the skin of the individual in need thereof, wherein the non-aqueous patch comprises a plaster comprising lidocaine, a dissolving agent, and an elastomer, wherein,
   the plaster comprises 0.5 to 7 mass % lidocaine and 1.435 to 9.1 mass % dissolving agent,
   the dissolving agent comprises dipropylene glycol and isostearic acid, and
   the isostearic acid is present in the plaster in an amount of 1.4 to 2.1 mass %.

2. The method of claim 1, wherein the elastomer consists of polyisobutylene and styrene isoprene rubber.

3. The method of claim 1, wherein the plaster comprises 10 mass % to 40 mass % of the elastomer.

4. The method of claim 1, wherein the plaster comprises 20 mass % to 40 mass % of the elastomer.

5. The method of claim 1, wherein the plaster further comprises a terpene resin.

6. The method of claim 1, wherein after application to a human for 12 hours, the amount of lidocaine remaining in the non-aqueous patch is 80% or less than the amount prior to application.

7. The method of claim 1, wherein the amount of lidocaine is 196 mg or less.

8. The method of claim 1, wherein the amount of lidocaine is 0.1 to 1 mg/cm$^2$ of the plaster.

9. The method of claim 1, wherein the lidocaine is completely dissolved in the dissolving agent.

10. The method of claim 1, wherein the lidocaine is completely dissolved in the plaster.

11. The method of claim 1, wherein the mass of the plaster is from about 60 to 200 g/m$^2$.

12. The method of claim 1, wherein the mass of the plaster is from 80 to 180 g/m$^2$.

13. The method of claim 1, wherein the non-aqueous patch further comprises a tackifier resin selected from the group consisting of terpene resin, rosin-based resin, alicyclic petroleum resin, phenolic resin and combinations thereof.

14. The method of claim 1, wherein the non-aqueous patch further comprises liquid paraffin.

15. The method of claim 1, wherein the plaster is held by a substrate selected from the group consisting of nonwoven fabric, woven fabric, knitted fabric or a combination thereof.

16. The method of claim 1, wherein the plaster is adhered to a polyester woven fabric.

17. The method of claim 1, wherein the pain is post-herpetic neuralgia.

18. The method of claim 1, wherein the non-aqueous patch is applied to the individual in need thereof for up to and including 12 hours.

* * * * *